United States Patent [19]

Davies et al.

[11] Patent Number: 5,714,462
[45] Date of Patent: Feb. 3, 1998

[54] ANTIVIRAL AGENT COMPRISING CD4 AND H2 HISTONE

[75] Inventors: Donald Selwyn Davies, Beaconsfield; Sunil Shaunak, Hertford; Nigel John Gooderham, Surrey; Robert John Edwards, Radlett, all of United Kingdom

[73] Assignee: ML Laboratories, England

[21] Appl. No.: 335,740

[22] PCT Filed: May 6, 1993

[86] PCT No.: PCT/GB93/00934

§ 371 Date: Dec. 30, 1994

§ 102(e) Date: Dec. 30, 1994

[87] PCT Pub. No.: WO93/21943

PCT Pub. Date: Nov. 11, 1993

[30] Foreign Application Priority Data

May 7, 1992 [GB] United Kingdom .................. 9209874

[51] Int. Cl.[6] .......................... A61K 38/16; A61K 39/21; C07K 1/00
[52] U.S. Cl. ........................... 514/8; 514/21; 530/395; 530/837; 530/838; 424/187.1; 424/188.1
[58] Field of Search .................. 514/8, 21; 530/395, 530/837, 838; 424/187.1, 188.1

[56] References Cited

PUBLICATIONS

Birnstiel et al, *Derwent Abstract* No. 92–333029 (DE 4110409, Mar. 29, 1991 or WO 9217210, Oct. 15, 1992).
Birnstiel et al, *Derwent Abstract* No. 91–369012 (DE 4110410, Mar. 29, 1991 or WO 9117773, Nov. 28, 1991).
Sandstrom et al, *Review Articles in Drugs*, vol. 34, pp.–373–390, 1987.
Haynes, *Science*, vol. 260, pp.–1279–1286, 28 May 1993.
Fox, *Bio/Technology*, vol. 12, p. 128, 12 Feb. 1994.
Brown, *The Washington Post*, Jun 10, 1993.
Fultz et al, *The Journal of Infectious Diseases*, vol. 163, pp. 441–447, Mar. 1993.
Green, *Scientific American*, pp.–99–105, Sep. 1993 issue.
Laurent–Crawford et al, *Virology*, vol. 185, pp. 829–839, 1991.

*Primary Examiner*—Cecilia J. Tsang
*Assistant Examiner*—Abdel A. Mohamed
*Attorney, Agent, or Firm*—Rodman & Rodman

[57] ABSTRACT

The invention provides an agent against HIV and/or related viruses, comprising CD4 or a CD4-like substance and an H2 histone or an H2 histone-like protein. The content of the CD4 or CD4-like substance is preferably less than the antivirally effective dose of that substance alone. The invention also provides an H2 histone or an H2-like protein, for use in a method of medical treatment, in particular against HIV and/or related viruses, and also for use in the manufacture of a pharmaceutical composition against HIV and/or related viruses.

3 Claims, No Drawings

ANTIVIRAL AGENT COMPRISING CD4 AND H2 HISTONE

BACKGROUND OF THE INVENTION

1. Field of the Invention

This invention relates to anti-viral agents, especially agents active against HIV-1 and related viruses.

2. Description of the Related Art

It is known that an initial stage of at least one mode of the infection of humans by RNA and DNA viruses involves attachment of the virus to the membrane of a human cell. In the case of HIV-1 and HIV-2, binding is between a cell surface glycoprotein, known as CD4, and a viral envelope protein known as gp120. Thus, CD4 acts as a cell surface receptor for the virus.

After attachment of the virus to the cell membrane the replication cycle of the virus involves a series of steps, one of which appears to be fusion of the viral envelope with the cell membrane. It might be expected that fusion depends solely on binding of gp120 to CD4. However, it is known that if the gene for human CD4 is transfected into CD4 negative HeLa.cells, these cells are then rendered susceptible to productive infection by HIV-1, whereas transfection of the same gene into mouse L-cells causes these cells to bind the virus but does not allow internalisation to occur. Also, experiments with VSV(HIV) pseudotypes have shown that HIV-1 binds to mouse L-cells transfected with human CD4 but is not internalised. Furthermore, it has been reported that CD4 negative cells from a wide range of human tissues can be infected by HIV-1; such infection is not blocked by preincubation of the cells with an anti-CD4 MAb (Leu 3a) or by incubation of the virus with sCD4. These observations cause us to postulate that fusion of the virus envelope with that of a CD4 positive cell requires the involvement of at least one other cell surface receptor, a "fusion receptor".

SUMMARY OF THE INVENTION

The present invention is based on our discovery that at least one such fusion receptor appears to be a cell surface protein having N-terminal homology to an H2 histone.

The invention provides an agent against human immunodeficiency virus (HIV) and/or related viruses comprising CD4 or a CD4-like substance (for example, CD4-IgFc immunoadhesins, CD4 V1-V2 domains, and CD4-derived peptides) and an H2 histone or H2 histone-like protein. The content of CD4 or CD4-like substance may be less than (for example, less than one-half of) the anti-virally effective dose of the CD4 or CD4-like substance alone.

DESCRIPTION OF THE PREFERRED EMBODIMENTS

In therapeutic use, the anti-viral agent of the invention is normally administered parenterally, for example intravenously. However, administration via the peritoneal cavity may be the most effective route in that it results in entry of at least some of the anti-HIV agent directly into the lymphatic system, where viral replication may be extensive.

The invention also provides the use of the agent described above against HIV and/or related viruses, the agent preferably being administered intraperitoneally, especially in a solution containing an osmotic agent which is a glucose polymer mixture, derived from the hydrolysis of starch, which includes at least 50% of glucose polymers of a degree of polymerisation greater than 12, as described in our British patent specification number 2154469A.

Further, the invention provides a pharmaceutical composition containing the agent described above together with an inert carrier or diluent; it also provides the agent of the invention for use in the manufacture of a pharmaceutical composition against HIV and/or related viruses.

The invention additionally provides a method of treatment of a human or animal subject carrying the HIV virus and/or a related virus, comprising administering to the subject a pharmaceutically effective amount of the agent of the invention. The CD4 or CD4-like substance and the H2 histone or H2 histone-like protein may be administered to a subject together or one after the other, in any order, although preferably with the CD4 or CD4-like material being administered before the H2 histone or H2 histone-like protein.

The invention also provides an H2 histone or an H2 histone-like protein, for use in a method of medical treatment of a human or animal body, in particular for use in a method of treatment of a human or animal subject carrying the HIV and/or a related virus; and an H2 histone or an H2 histone-like protein, for use in the manufacture of a pharmaceutical composition against HIV and/or related viruses.

It is known that some sulphated polysaccharides, such as dextran sulphate, heparin, heparin fragments, pentosan polysulphate and fucoidan, block infection by HIV-1 in vitro of human CD4+ and CD4− cells. It seemed possible that in the case of CD4+ cells this anti-viral activity involved interference with the attachment of the virus to the CD4 receptor on the host cell. However, it is now clear that most naturally occurring sulphated polysaccharides bind to sites which are separate from and/or additional to CD4. The manner in which sulphated polysaccharides act is therefore still uncertain and it is possible that they do not all have the same mode of action.

We have hypothesised that at least some of the anti-viral activity of sulphated polysaccharides in blocking HIV-1 infection is by acting on a "fusion receptor", a cell surface component which is present on all or most human cells and is critical for the fusion process. Some sulphated polysaccharides may also attach themselves to viral gp120, but any antiviral activity resulting from this interaction is probably of less importance than their activity in blocking the fusion receptor.

To investigate this hypothesis, we carried out a number of experiments using dextrin sulphate as the anti-HIV agent.

Dextrin is a mixture of glucose polymers, in which the glucan units have predominantly alpha-1,4 glucosidic bonds. The dextrin sulphate used in our experiments was a 2-sulphated dextrin sulphate with a weight average molecular weight of about 27,000. It had a sulphur content of 12% by weight, equivalent to one sulphate group per glucose residue.

In tissue culture experiments we have found that dextrin sulphate blocks infection of CD4+ cell lines (M8166, HPB ALL) by a variety of HIV-1 laboratory isolates (IIIb, RF, MN) at an inhibitory concentration of 6–12 ug/ml (230–460 nM). We have also shown that dextrin sulphate blocks infection of several CD4− cells; TE671 HH24 (rhabdomyosarcoma), U251 SP HH51, U138 HH 54 (glia) and HT29/7 (colorectal carcinoma). Infection is not prevented by preincubating the cells with Leu 3a or the virus with sCD4.

These tissue culture experiments appeared to support our hypothesis that dextrin sulphate blocked HIV-1 infection by acting on a fusion receptor. We then carried out receptor-ligand binding studies, and found no evidence to suggest that dextrin sulphate binds to CD4. Preincubation of CD4+ cells with Leu 3a does not alter the binding constants, and transfection of CD4 into HeLa cells reduces rather than increases dextrin sulphate binding. We have also found that pretreatment of HPB ALL cells with trypsin abolishes dextrin sulphate binding. In contrast, pretreatment with neuraminidase does not affect binding, suggesting a protein binding site. These results suggest that the same dextrin sulphate binding site is present on human CD4+ and CD4− human cells.

We have carried out ligand-blot experiments with a view to identifying the nature of the dextrin sulphate binding site. HPB ALL cell membranes were prepared and the proteins separated using 12.5% SDS-PAGE gels. After blotting to nitrocellulose filters, they were probed with tritiated dextrin sulphate. Binding of the labelled dextrin sulphate to bands which correspond to proteins of molecular weights of 29 kDa and 17 kDa was observed; binding of the labelled dextrin sulphate to these two bands could be displaced with an excess of cold dextrin sulphate. Most of the displaceable binding was to the 17 kDa site.

It appears that one or other of the proteins to which dextrin sulphate binds may constitute the fusion receptor or part of the fusion receptor. Determination of the N-terminal sequence of two of the proteins of interest, the 17 kDa proteins, revealed that one of them (with N-terminal sequence PEPAKSAPAPKKGXKKXVTKA) showed homology with histone H2B and the other (with N-terminal sequence ARTKQTARKSTGGKAPRKQLAT) with histone H3.1. There has been no previous evidence to suggest that histones were in any way involved in the HIV infection cycle. Histones are a group of strongly basic proteins.

We now believe that a histone or a histone-like protein may constitute the fusion receptor postulated above. It is known that as nucleoproteins H2A, H2B and H3.1 can bind DNA and RNA. We therefore believe that one or all of these histones or histone-like proteins on the cell surface interacts with viral RNA, and that this leads to entry of the virus into the cell. H2A and H2B are also known to bind heparin, a sulphated polysaccharide, so it is reasonable to assume that these histones will bind some other sulphated polysaccharides.

HIV infection of CD4 positive cells appears to be initiated by the binding of the viral envelope protein gp120 to the cell surface protein CD4, following which there is a temperature-dependent conformational change which exposes the hydrophobic, N-terminus of gp41 which is believed to fuse with the cell membrane. The mechanisms underlying fusion remain to be defined. Morphological studies, however, suggest that the process of fusion involves spontaneous disintegration of the core and the release of viral RNA into the cytoplasm.

Our results suggest a mechanism of viral entry in which cell surface histones interact with a component of HIV-1 following the conformational change induced by binding to CD4. We have not established whether cell surface histones interact with a core or an envelope component of HIV-1. However, the known anti-HIV activity of guanosine oligonucleotides and their ability to bind in a specific manner leads us to suggest that guanosine-rich regions within viral RNA may be able to interact with cell surface histones. The histone-RNA complex formed could then undergo micropinocytosis and internalisation.

We think it possible that dextrin sulphate and guanosine oligonucleotides block HIV infection by binding to cell surface histones and preventing their interaction with gp41.

The mechanism postulated above implies that the initial interaction of gp120 with CD4 results in the uncoating of the virus particle. Other, as yet undefined, cell surface receptors (e.g. proteinases) may be involved in this process.

Our experimental work has shown that neither calf thymus histones (H1, H2A, H2B, H3 or H4) nor other basic proteins (i.e. lysozyme and alpha-bungarotoxin) have any intrinsic anti-HIV-1 activity. However, when C8166 cells preincubated with histone H2A or H2B were added to HIV-1 (IIIB) which had first been incubated with sub-inhibitory concentrations of soluble CD4, the cells did not become infected. The amount of soluble CD4 required to inhibit infection was progressively reduced with increasing concentrations of histone H2A or H2B. In contrast, a similar antiviral effect was not seen in combinations of each of the histones H1, H3, H4, lysozyme and alpha-bungarotoxin with soluble CD4.

Example 1, below, describes the results of experiments to examine the anti-viral activity of histones H2A and H2B, alone and together with soluble CD4.

EXAMPLE 1

Calf thymus histones were used for these experiments because they are identical or highly homologous with human histones. C8166 cells were incubated with histone H2A or H2B (Boehringer Mannheim, Germany) for one hour at 37° C. At the same time, HIV-1 (IIIb; $10^{2.5}$ culture infectious doses) was incubated with sCD4 (baculovirus) for 1 hour at 37° C. The symbol (+) represents no reduction in the number of syncytia counted in C1866 cells as compared with controls. The symbol (−) represents a 90% reduction in the number of syncytia as compared with controls. Tables I and II summarise the results from three separate experiments.

In the absence of CD4, the histones are inactive even at 62.5 ug/ml. In the absence of the histone, CD4 inhibited HIV-1 infection at 0.5 ug/ml; the activity of CD4 was enhanced by the presence of histone, such enhancement being increased with increasing concentration of the histone.

TABLE I

| Histone H2A (ug/ml) | Soluble CD4 (ug/ml) | | | | | |
|---|---|---|---|---|---|---|
| | 0.5 | 0.375 | 0.25 | 0.188 | 0.125 | 0 |
| 62.5 | − | − | − | − | − | + |
| 46.9 | − | − | − | − | + | + |
| 31.25 | − | − | − | − | + | + |
| 23.4 | − | − | − | + | + | + |
| 15.6 | − | − | − | + | + | + |
| 11.7 | − | − | − | + | + | + |
| 7.8 | − | − | + | + | + | + |
| 5.9 | − | − | + | + | + | + |
| 3.9 | − | − | + | + | + | + |
| 2.9 | − | + | + | + | + | + |
| 1.95 | − | + | + | + | + | + |
| 0.0 | − | + | + | + | + | + |

TABLE II

| Histone H2B (ug/ml) | Soluble CD4 (ug/ml) | | | | | |
|---|---|---|---|---|---|---|
| | 0.5 | 0.375 | 0.25 | 0.188 | 0.125 | 0 |
| 62.5 | − | − | − | − | − | + |
| 46.9 | − | − | − | − | − | + |
| 31.25 | − | − | − | − | + | + |
| 23.4 | − | − | − | + | + | + |
| 15.6 | − | − | − | + | + | + |
| 11.7 | − | − | − | + | + | + |
| 7.8 | − | − | + | + | + | + |

TABLE II-continued

| Histone H2B (ug/ml) | Soluble CD4 (ug/ml) | | | | | |
|---|---|---|---|---|---|---|
| | 0.5 | 0.375 | 0.25 | 0.188 | 0.125 | 0 |
| 5.9 | − | − | + | + | + | + |
| 3.9 | − | − | + | + | + | + |
| 2.9 | − | + | + | + | + | + |
| 1.95 | − | + | + | + | + | + |
| 0.0 | − | + | + | + | + | + |

From these tests it appears that the histones themselves have no anti-HIV activity at relatively high concentrations. However, they boost the activity of CD4, so that anti-HIV compositions which rely for their activity on the presence of CD4 can be formulated with a lower CD4 content for the same activity if they contain one of these histones in addition to CD4. It is believed that the srCD4 causes a conformational change in the Viral envelope of the virus from the capsid, and infection is then blocked by H2A and/or H2B. Enhancement of the anti-HIV activity of CD4 is not seen with other histones or with other basic proteins (lysozyme and alpha bungarotoxin).

We claim:

1. A composition comprising CD4 or a CD4-like substance and an H2 histone or an H2 histone-like protein and a pharmaceutically acceptable carrier.

2. The composition of claim 1 wherein the histone is histone H2B.

3. The composition of claim 1 wherein the histone is histone H2A.

* * * * *